US009297779B2

(12) United States Patent
Miwa et al.

(10) Patent No.: US 9,297,779 B2
(45) Date of Patent: Mar. 29, 2016

(54) EXHAUST GAS SENSOR

(71) Applicants: Tomohiro Miwa, Toyota (JP); Sumio Kamiya, Toyota (JP); Hirotaka Sakakibara, Toyota (JP); Tomoaki Shinma, Toyota (JP)

(72) Inventors: Tomohiro Miwa, Toyota (JP); Sumio Kamiya, Toyota (JP); Hirotaka Sakakibara, Toyota (JP); Tomoaki Shinma, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 14/405,635

(22) PCT Filed: Jul. 24, 2013

(86) PCT No.: PCT/IB2013/001604
§ 371 (c)(1),
(2) Date: Dec. 4, 2014

(87) PCT Pub. No.: WO2014/024018
PCT Pub. Date: Feb. 13, 2014

(65) Prior Publication Data
US 2015/0153304 A1 Jun. 4, 2015

(30) Foreign Application Priority Data
Aug. 7, 2012 (JP) ................... 2012-175335

(51) Int. Cl.
G01N 27/409 (2006.01)
G01N 27/407 (2006.01)

(52) U.S. Cl.
CPC .......... G01N 27/409 (2013.01); G01N 27/4077 (2013.01)

(58) Field of Classification Search
CPC ..................... G10N 27/406; G10N 27/41
See application file for complete search history.

(56) References Cited

U.S. PATENT DOCUMENTS

| 4,164,462 A | 8/1979 | Ichikawa et al. |
| 4,383,906 A * | 5/1983 | Sano ................. G01N 27/4078 204/412 |
| 2009/0014330 A1 | 1/2009 | Sugaya et al. |
| 2011/0220496 A1 | 9/2011 | Oya et al. |

FOREIGN PATENT DOCUMENTS

| CN | 1150447 A | 5/1997 |
| EP | 0 366 863 A2 | 5/1990 |
| EP | 1 445 607 A1 | 8/2004 |
| EP | 1 662 253 A2 | 5/2006 |
| JP | 58-019553 A | 2/1983 |

(Continued)

OTHER PUBLICATIONS

International Search Report and Written Opinion for corresponding International Patent Application No. PCT/IB2013/001604 mailed Oct. 28, 2013.

*Primary Examiner* — J. Christopher Ball
(74) *Attorney, Agent, or Firm* — Sughrue Mion, PLLC

(57) ABSTRACT

An exhaust gas sensor (100) is configured to detect an oxygen concentration or air-fuel ratio in exhaust gas of an internal combustion engine. The exhaust gas sensor includes a sensor element (10) and a glass coating film (20). The sensor element is configured to detect an oxygen concentration or air-fuel ratio in the exhaust gas sensor. The glass coating film (20) is formed on at least part of a surface of the sensor element and capable of absorbing a Mn component contained in the exhaust gas at 700° C. The internal combustion engine uses a fuel having a Mn concentration in excess of 20 ppm.

4 Claims, 5 Drawing Sheets

(56) References Cited

FOREIGN PATENT DOCUMENTS

| | | |
|---|---|---|
| JP | 61-155853 A | 7/1986 |
| JP | 2007-163272 A | 6/2007 |
| JP | 2011-209280 A | 10/2011 |
| JP | 2011-252894 A | 12/2011 |
| JP | 2014-035221 A | 2/2014 |
| WO | 9523836 A1 | 9/1995 |
| WO | 2014/024017 A | 2/2014 |

* cited by examiner

RELATED ART

EXHAUST GAS SENSOR

BACKGROUND OF THE INVENTION

1. Field of the Invention

The invention relates to an exhaust gas sensor.

2. Description of Related Art

Gas sensors that utilize sensor elements have been used conventionally in order to detect specific gases in the atmosphere. Such gas sensors, for instance, can detect the concentration of a specific gas component such as hydrocarbons (HC), oxygen ($O_2$) or the like that are present in the exhaust gas of automobiles. To that end, one such gas sensor is provided in the exhaust passage of an internal combustion engine, for instance an automobile engine. The gas sensor is used to control an exhaust gas control apparatus. Conventional oxygen sensor elements that detect the concentration of oxygen in exhaust gas include, for instance, oxygen concentration-electromotive force sensors that have a $ZrO_2$ solid electrolyte.

As illustrated in FIG. 9, an oxygen sensor element 90, in the form of a bottomed cylinder, is configured through sequential layering of an inner electrode 94a, a solid electrolyte layer 92, an outer electrode 94b, and a diffusion resistance layer 96. A heater 97 is inserted inward of the inner electrode 94a. Exhaust gas reaches the outer electrode 94b through micro-holes in the diffusion resistance layer 96, and a sensor output is obtained between the outer electrode 94b and the inner electrode 94a. The diffusion resistance layer 96 is formed of a porous ceramic coating, with a view to imparting a function of limiting the flow rate of exhaust gas that reaches the outer electrode 94b and of protecting the outer electrode 94b.

The exhaust gas contains noxious substances that include components present in oil, for instance P, Ca or Zn, as well as gasoline additive components such as K or Na. Therefore, in cases where such a sensor element is used in an exhaust gas sensor for automobiles, a problem may arise in that the sensor element may become contaminated by these noxious substances. To address this problem, it has been proposed to cover the periphery of the sensor element with a porous protective layer (trap layer) 98 (FIG. 9). In the above technology, noxious substances in the exhaust gas become adsorbed onto the protective layer 98. As a result, this allows suppressing intrusion of the noxious substances into the sensor element. Japanese Patent Application Publication No. 2011-252894 (JP 2011-252894 A) is an instance of related art pertaining to such gas sensors.

SUMMARY OF THE INVENTION

Improving thermal efficiency by increasing the compression ratio of the engine is an effective way of improving fuel economy in an automobile. However, knocking occurs readily in engines of high compression ratio, and hence the engine requires a high-octane fuel. Studies in recent years have addressed the addition of Mn-containing additives to fuel in order to increase the octane number of fuel.

The inventors focused on the phenomenon of delayed (worsened) sensor response in internal combustion engines that utilize a fuel containing the abovementioned Mn component. The inventors analyzed in detail the influence that the Mn component in the fuel exerts on sensor response, and arrived at the findings below.

When becoming adhered to the sensor element, the Mn component in fuel is deposited in the form of a Mn oxide. When, in that state, exhaust gas having a high oxygen concentration flows into the gas sensor, the Mn oxide adhered on the sensor element becomes oxidized, and oxygen in the exhaust gas is consumed as the oxidation reaction $Mn_3O_4 + O_2 \rightarrow Mn_2O_3$ progresses. As a result, the oxygen concentration in the exhaust gas that reaches the sensor electrode becomes lower than the actual one. The abovementioned oxidation reaction continues, in that state, until completion. Accordingly, the sensor value takes on a value that is lower than the actual oxygen concentration until the abovementioned oxidation reaction is over. Thus, the response in a case where exhaust gas of high oxygen concentration flows into the gas sensor becomes delayed.

On the other hand, when exhaust gas of low oxygen concentration flows into the gas sensor, the Mn oxide adhered to the sensor element becomes reduced, and oxygen is released into the exhaust gas as the opposite reaction proceeds, i.e. the reduction reaction $Mn_2O_3 \rightarrow Mn_3O_4 + O_2$. As a result, the oxygen concentration in the exhaust gas that reaches the sensor electrode is higher than the actual one. The state where the oxygen concentration is higher than the actual one continues until completion of the abovementioned reduction reaction.

Accordingly, the sensor value takes on a value that is higher than the actual oxygen concentration, until the abovementioned reduction reaction is over. The response in a case where exhaust gas of low oxygen concentration flows into the gas sensor becomes thus delayed. In this way, the response of the sensor becomes delayed through the occurrence of oxygen absorption and release (oxygen storage capacity, OSC) reaction that accompanies changes in the valence of Mn. A mechanism for effectively preventing the abovementioned OSC is accordingly required.

The invention provides an exhaust gas sensor that is based on the above findings.

The exhaust gas sensor in an aspect of the invention is configured to detect an oxygen concentration or air-fuel ratio in exhaust gas of an internal combustion engine. The exhaust gas sensor has a sensor element and a glass coating film. The exhaust gas sensor includes a sensor element and a glass coating film. The sensor element is configured to detect an oxygen concentration or air-fuel ratio in the exhaust gas sensor. The glass coating film is formed on at least part of a surface of the sensor element and is capable of absorbing a Mn component contained in the exhaust gas at 700° C. The internal combustion engine uses a fuel having a Mn concentration in excess of 20 ppm.

In the exhaust gas sensor thus configured, the glass coating film capable of absorbing an Mn component in exhaust gas is formed on at least part of a surface of the sensor element. The Mn component adhered to the glass coating film undergoes solid-state diffusion into the glass coating film at times of high temperature, and becomes incorporated in the interior of the glass coating film. Therefore, Mn and exhaust gas do not come into direct contact with each other, and hence oxygen storage capacity (OSC) that accompanies changes in the valence of Mn is suppressed, and sensor response delay is unlikelier to occur.

In the aspect of the invention, the exhaust gas sensor may be used in order to detect an oxygen concentration or air-fuel ratio in the exhaust gas of the internal combustion engine that utilizes a fuel having a Mn concentration in excess of 20 ppm. Herein, Mn adheres readily onto the sensor element and sensor response delay is likely to occur in an exhaust gas sensor for detecting the oxygen concentration or air-fuel ratio in the exhaust gas of an engine that utilizes such fuels having a high Mn concentration. Therefore, the exhaust gas sensor of one aspect of the invention, which allows effectively preventing the abovementioned sensor response delay, may be used as exhaust gas sensors for detecting the oxygen concentration or air-fuel ratio in the exhaust gas of internal combustion engines that utilize fuels having a high Mn concentration, such as the abovementioned ones.

In the aspect of the invention, the glass coating film may be made up of borosilicate glass containing at least Si and B. Borosilicate glass having Si and B exhibits the property of readily absorbing Mn, and hence may be used as a glass coating film material in the aspect of the invention.

In the aspect of the invention, the borosilicate glass may be made up of Si, B, Al, Ba and R as main constituents. R is at least one from among Li, Na and K. Then, a mass ratios of main components of the borosilicate glass, in terms of oxide, with an entirety of the borosilicate glass as 100 mass %, may be: $SiO_2$ 30 mass % to 45 mass %; $B_2O_3$ 10 mass % to 20 mass %; $Al_2O_3$ 1 mass % to 10 mass %; BaO 20 mass % to 30 mass %; $R_2O$ 2 mass % to 10 mass %. Furthermore, a total of the main components may be 70 mass % or more. Borosilicate glass having the above composition exhibits the property of readily absorbing Mn, and hence may be used as a glass coating film material in the aspect of the invention.

In the aspect of the invention, the sensor element may be formed of a stack of a solid electrolyte layer, a heater layer and a porous diffusion resistance layer. The pair of electrodes is provided on either side of the solid electrolyte layer. The heater layer includes a heating element that generates heat through energization. The diffusion resistance layer lets the exhaust gas through in such a manner that the exhaust gas is introduced into either of the pair of electrodes. Furthermore, the glass coating film may be formed, on the surface of the sensor element, at a region excluding the diffusion resistance layer. The above configuration enables uptake of Mn into the glass coating film while allowing the gas sensor to operate properly.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Embodiments of the invention are explained next. Any features other than the features specifically set forth in the description and which may be necessary for carrying out the invention can be regarded as instances of design matter for a person skilled in the art on the basis of related arts in the technical field in question. The invention may be carried out thus on the basis of the features disclosed in the description and on the basis of common technical knowledge in the technical field in question.

Figure 1:
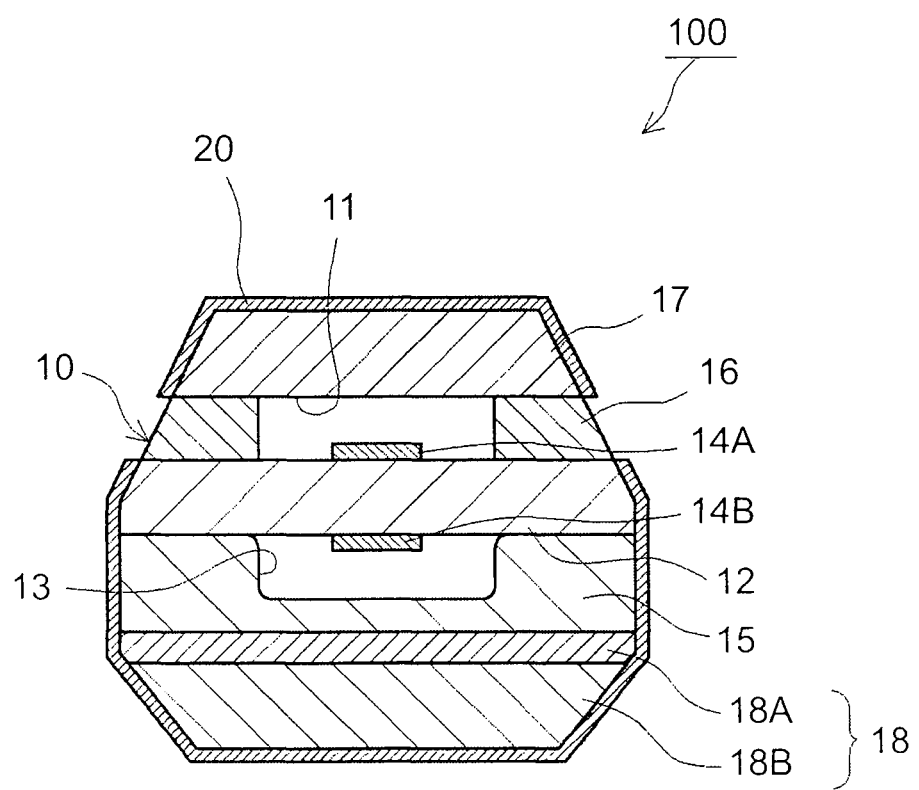
FIG. 1 is a cross-sectional diagram illustrating schematically an exhaust gas sensor according to a first embodiment of the invention.

A gas sensor, as a first embodiment, is an exhaust gas sensor capable of detecting an oxygen concentration or air-fuel ratio in exhaust gas. The exhaust gas sensor is used in order to detect the oxygen concentration or air-fuel ratio in the exhaust gas of an internal combustion engine that utilizes a fuel (typically, gasoline) the Mn concentration whereof exceeds 20 ppm. The structure of an exhaust gas sensor 100 will be explained with reference to FIG. 1. FIG. 1 is a schematic diagram illustrating, in a cross-section, an example of the configuration of a main portion of the exhaust gas sensor 100 of the first embodiment.

As illustrated in FIG. 1, the exhaust gas sensor 100 has a sensor element 10 that detects an oxygen concentration or air-fuel ratio, and a glass coating film 20 that is formed on at least part of the surface of the sensor element 10.

A gas sensor, as a first embodiment, is an exhaust gas sensor capable of detecting an oxygen concentration or air-fuel ratio in exhaust gas. The exhaust gas sensor is used in order to detect the oxygen concentration or air-fuel ratio in the exhaust gas of an internal combustion engine that utilizes a fuel (typically, gasoline) the Mn concentration whereof exceeds 20 ppm. The structure of an exhaust gas sensor 100 will be explained with reference to FIG. 1. FIG. 1 is a schematic diagram illustrating, in a cross-section, an example of the configuration of a main portion of the exhaust gas sensor 100 of the first embodiment.

The solid electrolyte layer 12 is made up of a solid electrolyte having oxygen ion conductivity. Examples of such a solid electrolyte include, for instance, zirconia (for example, yttria-stabilized zirconia (YSZ)).

The measurement electrode 14A is formed outward of the solid electrolyte layer 12. A measurement gas space 11, into which exhaust gas can be introduced, and having, as one wall, the solid electrolyte layer 12, is formed further outward than measurement electrode 14A.

The measurement gas space 11 is defined by the solid electrolyte layer 12, the diffusion resistance layer 16 and the shielding layer 17. The shielding layer 17 has a gas-impervious internal structure, and is made up of alumina in the first embodiment. The diffusion resistance layer 16 is provided at positions that define the measurement gas space 11 around the measurement electrode 14A (herein, at both ends of the measurement gas space 11 in the width direction), in order to restrict the introduction amount of exhaust gas into the measurement electrode 14A. The diffusion resistance layer 16 is a porous body through which exhaust gas is introduced into the measurement gas space 11. Materials that can make up a porous body, for instance, alumina, zirconia, ceria or the like may be used as the material of the diffusion resistance layer 16.

The reference electrode 14B is formed inward of the solid electrolyte layer 12. A reference gas space 13, into which a reference gas such as the atmosphere or the like can be introduced, is formed so as to surround the reference electrode 14B. The reference gas space 13 is defined by the solid electrolyte layer 12 and a protective layer 15. The protective layer 15 has a gas-impervious internal structure, and is herein made up of alumina. The reference electrode 14B and the measurement electrode 14A are both made up of a precious metal having high catalytic activity, for instance platinum or the like.

The heater layer 18 is made up of an insulating base 18B having alumina as a main constituent, and the heating resistor 18A that is stacked on the insulating base 18B. The solid electrolyte layer 12 made up of zirconia or the like has an insulation at normal temperature, but in high-temperature environments the solid electrolyte layer 12 becomes activated and exhibits high oxygen ion conductivity. The heater layer 18 serves as a heating region of the solid electrolyte layer 12. Heating by the heater layer 18 is controlled in such a manner that the activation temperature is reached in the heating region. In the embodiment, the heater layer 18 is disposed outward of the protective layer 15, on the reference electrode 14B side of the solid electrolyte layer 12. The heating resistor 18A is made up of a resistor, for instance of platinum or the like.

The glass coating film 20 is formed on at least part of the surface of the sensor element 10 that is made up of the solid electrolyte layer 12, the diffusion resistance layer 16 and the heater layer 18 described above. The glass coating film 20 is formed on all regions of the surface of the sensor element 10, excluding the porous diffusion resistance layer 16. The glass coating film 20 is made up of, as a main constituent, at least a glass composition that can absorb a Mn component in exhaust gas at 500° C. That is, the glass coating film 20 is provided in order to take up the Mn component that is present in the exhaust gas. The Mn component adhered to the glass coating film 20 undergoes solid-state diffusion into the glass coating film 20 depending on the temperature during heating of the sensor (500° C. to 600° C. in the case of an oxygen sensor, 700° C. to 800° C. in the case of an air-fuel ratio sensor), and becomes incorporated in the interior of the glass coating film 20. The likelihood of direct contact between the exhaust gas and the Mn component adhered to the sensor element 10 is reduced as a result.

The thickness of the glass coating film 20 disclosed herein is not particularly limited, but is appropriately of about 50 μm or greater, and ranges preferably from 50 μm to 100 μm. A sufficient amount of the Mn component can be taken up into the glass coating film 20 if the thickness of the glass coating film 20 is 50 μm or greater.

The glass coating film 20 may be made up of, as a main constituent, a glass composition that can absorb a Mn component in exhaust gas at least at 700° C. In the present embodiment, the glass coating film 20 is a glass coating film that has, as a main constituent, borosilicate glass containing at least Si and B, and that contains $SiO_2$ and $B_2O_3$ as essential components. The greater the proportion of $B_2O_3$ in the mixing ratio between $SiO_2$ and $B_2O_3$ in the borosilicate glass, the more readily Mn tends to be absorbed. In terms of mass ratio, for instance, the mixing ratio $B_2O_3/SiO_2$ may range from 0.25 to 0.5 (preferably, from 0.3 to 0.5, more preferably from about 0.35 to about 0.5). The Mn adhered to the glass coating film 20 made up of the borosilicate glass can be better absorbed by the glass coating film 20 when $B_2O_3/SiO_2$ lies within the above ranges.

Besides these essential components, the glass coating film 20 may contain various other oxide components ($Al_2O_3$, BaO, $R_2O$ and the like), in accordance with the intended purpose. Preferably, for instance, the borosilicate glass that is used in the present embodiment has an oxide component that allows further enhancing Mn absorbability. Also, it is preferably that a glass composition is used that has a stable composition and that does not melt readily in the high-temperature region at which the exhaust gas sensor is used (500° C. to 600° C. in the case of an oxygen sensor, 700° C. to 800° C. in the case of an air-fuel ratio sensor). Furthermore, it is preferably that a below-described glaze slurry for forming the glass coating film 20 has an oxide component that allows adjusting the viscosity of the slurry in such a manner that the slurry can be readily applied onto the surface of the sensor element. Any borosilicate glass that satisfies such conditions may be used, without particular limitations. Examples of borosilicate glass include, for instance, borosilicate glass made up of silicon (Si), boron (B), aluminum (Al), barium (Ba) and an alkali metal (R), as main constituents. Herein, R denotes one, two or more alkali metal elements from among Li, Na and K. Preferably, at least two elements from among Li, Na and K are used, and particularly preferably, all of Li, Na and K are used.

Preferably, for instance, $SiO_2$ is 30 mass % to 45 mass %, $B_2O_3$ is 10 mass % to 20 mass %, $Al_2O_3$ is 1 mass % to 10 mass %, BaO is 20 mass % to 30 mass % and $R_2O$ is 2 mass % to 10 mass % in the mass composition of the glass matrix as a whole, and the total of the foregoing main components is 70 mass % or more. Further preferably, the total of the above main components is 80 mass % or more in the whole glass. The borosilicate glass having the above oxide components in the abovementioned mass composition absorbs Mn readily, and is stable in the high-temperature region at which the exhaust gas sensor is used. Therefore, the borosilicate glass can be suitably used as the glass composition of the embodiment of the invention.

Preferably, such borosilicate glass contains any one, two or more oxides from among MgO, CaO and SrO. Herein, MgO, CaO and SrO, which are alkaline earth metal oxides, are optionally added components. Incorporating these components results in a glass matrix made up of a multi-component system. The chemical and physical characteristics of the glass matrix can be enhanced as a result. The content of these oxides in the glass composition as a whole is preferably zero (no addition), or 10 mass % or less. Preferably, for instance, the total amount of CaO plus SrO is 8 mass % or less (for instance, 0.1 mass % to 8 mass %) of the glass composition as a whole.

Preferably, the borosilicate glass further contains $La_2O_3$. Herein, $La_2O_3$ is an optionally added component. Incorporating this component results in a glass matrix made up of a multi-component system. The chemical and physical characteristics of the glass matrix can be enhanced as a result. The content of $La_2O_3$ in the glass composition as a whole is preferably zero (no addition), or 2 mass % or less.

Preferably, the borosilicate glass further contains $ZrO_2$. Herein, $ZrO_2$ is an optionally added component. Incorporating this component results in a glass matrix made up of a multi-component system. The chemical and physical characteristics of the glass matrix can be enhanced as a result. The content of $ZrO_2$ in the glass composition as a whole is preferably zero (no addition), or 2 mass % or less.

Besides the above-described components, other components (for instance, ZnO, NiO, SnO, CoO, $MoO_2$, $HfO_2$ and $Y_2O_3$) that are not essential in the embodiment of the invention may be added in accordance with the intended use. These components as well contribute to diversifying the glass constitution.

In the technology disclosed herein, the term "glass coating film" conceptually includes also aspects in which a crystalline phase is present in a part of the glass coating film. A preferred aspect of the technology disclosed herein may be, for instance, a glass coating film that has an amorphous phase of the above oxide components as a main constituent, and also has a crystalline phase of $K(Si_3Al)O_8$, $Ca(Mg_{0.7}Al_{0.3})(Si_{1.7}Al_{0.3})O_6$ or the like. By virtue of the presence of such a crystalline phase in the glass coating film, Mn undergoes solid-state diffusion yet more readily in the glass coating film. In a preferred aspect, the crystalline phase may include at least one crystalline phase from among $K(Si_3Al)O_8$ and $Ca(Mg_{0.7}Al_{0.3})(Si_{1.7}Al_{0.3})O_6$. The crystalline phase may be mixed into (dispersed in) the amorphous phase, or may be unevenly distributed, or precipitated, in the vicinity of the surface of the glass coating film.

The glass coating film 20 may be formed as described below. Firstly, compounds for obtaining the various oxide components that make up the glass component (glass matrix) of the glass coating film 20 are prepared in the form of glass starting materials (glaze) powders. As the case may require, the glass starting materials (glaze) powders may further include other additives. Typically, a mixture resulting from mixing the above compounds and these additives is prepared as the glass starting materials (glaze) powder. The compounds for obtaining various oxide components may be, for instance, industrial products, reagents, or various mineral materials that include oxides, hydroxides, carbonates, sulfates, nitrates, complex oxides or the like containing respective components. These glass starting material powders are added and mixed so as to obtain a desired composition, and thereafter a glaze slurry is prepared wherein the resulting mixture is dispersed in an appropriate solvent (for instance, water). The glaze slurry is applied onto the surface of the sensor element, and is fired, to form thereby the glass coating film 20. The glaze slurry may contain an appropriate amount of a clay mineral or organic binder, with a view to, for instance, improving the shape retention of the coating.

Ordinary coating means may be used, without any limitations, in the operation of applying the glaze slurry onto the surface of the sensor element 10. For instance, the glaze slurry may be applied through coating of a predetermined amount of the glaze slurry onto the surface of the sensor element 10 that excludes the diffusion resistance layer 16, using an appropriate coating apparatus (spray atomizer, roller or the like). Thereafter, the glass coating film 20 may be formed on the surface of the sensor element 10 through firing (baking) of the coating, using appropriate firing means. The firing temperature ranges from about 900° C. to about 1000° C., preferably from about 920° C. to about 980° C. The time over which the firing temperature (highest firing temperature) is held, depending on the firing temperature, within a range from about 0.5 hours to about 2 hours, preferably from about 1 hour to about 1.5 hours. The abovementioned firing may be performed in an air atmosphere.

In the exhaust gas sensor 100 thus configured, the glass coating film 20 capable of absorbing an Mn component in exhaust gas is formed on at least part of the surface of the sensor element 10. The Mn component adhered to the glass coating film 20 undergoes solid-state diffusion into the glass coating film 20 at times of high temperature, and becomes incorporated in the interior of the glass coating film 20. The likelihood of direct contact between the exhaust gas and the Mn component adhered to the sensor element 10 is reduced as a result. Accordingly, there is suppressed the OSC reaction that accompanies changes in the valence of the Mn that is adhered sensor element 10, and there is reduced the delay in the change of oxygen concentration in the exhaust gas that reaches the measurement electrode 14A. Sensor response delay can be reduced as a result.

In the above embodiment, the sensor element 10 is formed of a stack of the solid electrolyte layer 12, the heater layer 18 and the porous diffusion resistance layer 16. The measurement electrode 14A and the reference electrode 14B are respectively provided on either side of the solid electrolyte layer 12. The heater layer 18 has the heating resistor 18A that generates heat when energized. The diffusion resistance layer 16 lets exhaust gas through in such a manner that the exhaust gas is introduced into the measurement electrode 14A. The glass coating film 20 is formed, on the surface of the sensor element 10, at a region excluding the diffusion resistance layer 16. Therefore, the glass coating film 20 does not prevent introduction of exhaust gas into the measurement electrode 14A. As a result, the Mn component can be taken up into the interior of the glass coating film 20 while the gas sensor 100 can operate properly.

Preferably, the technology disclosed herein may be used in exhaust gas sensors for detecting the oxygen concentration or air-fuel ratio in the exhaust gas of an engine that utilizes fuel with high Mn concentration, with a content of Mn in excess of 20 ppm. The fuel with high Mn concentration may be, for instance, a fuel the Mn concentration whereof is 20 ppm or higher, 40 ppm or higher, typically 60 ppm or higher, preferably 100 ppm or higher, or further preferably 200 ppm or higher. Typically, the fuel of high Mn concentration has a Mn concentration of 60 ppm or higher. The Mn component adheres readily onto the sensor element of an exhaust gas sensor for detecting the oxygen concentration or air-fuel ratio in the exhaust gas of an engine that utilizes such fuels having a high Mn concentration, and sensor response delay due to OSC that accompanies changes in the valence of Mn is likely to occur. Therefore, the exhaust gas sensor 100 of the embodiment of the invention, which allows effectively preventing sensor response delay due to the abovementioned OSC, can be suitably used, in particular, in engines that utilize fuels having a high Mn concentration, such as the abovementioned ones.

Experimental examples relating to the invention are explained next, but the invention is not meant to be limited to the features described in the Experimental examples.

In Example 1, starting material powders of the glass coating film 20 having borosilicate glass were added and mixed at predetermined ratios, as given in Tables 1-1 and 1-2. Thereafter, the resulting mixture was dispersed in water, to prepare a glaze slurry. The glaze slurry was applied onto the surface of the sensor element 10, followed by firing at 950° C. for 1 hour. An exhaust gas sensor 100 was thus obtained in which the glass coating film 20 was formed on the surface of the sensor element 10.

TABLE 1-1

| Composition (mass %) | | | | | | |
|---|---|---|---|---|---|---|
| $SiO_2$ | $B_2O_3$ | $Al_2O_3$ | BaO | $Li_2O$ | $Na_2O$ | $K_2O$ |
| 40.45 | 12.10 | 4.93 | 24.75 | 0.51 | 0.39 | 1.64 |
| MgO | CaO | $SrO_2$ | $La_2O_3$ | $ZrO_2$ | SnO | |
| 1.83 | 7.00 | 0.30 | 1.93 | 1.68 | 0.62 | |
| Total: 98.13 mass % | | | | | | |

TABLE 1-2

| Minor component composition (mass %) | | | | | |
|---|---|---|---|---|---|
| ZnO | CoO | NiO | $MoO_2$ | $Y_2O_3$ | $HfO_2$ |
| Total: 1.87 mass % | | | | | |

Figure 2:
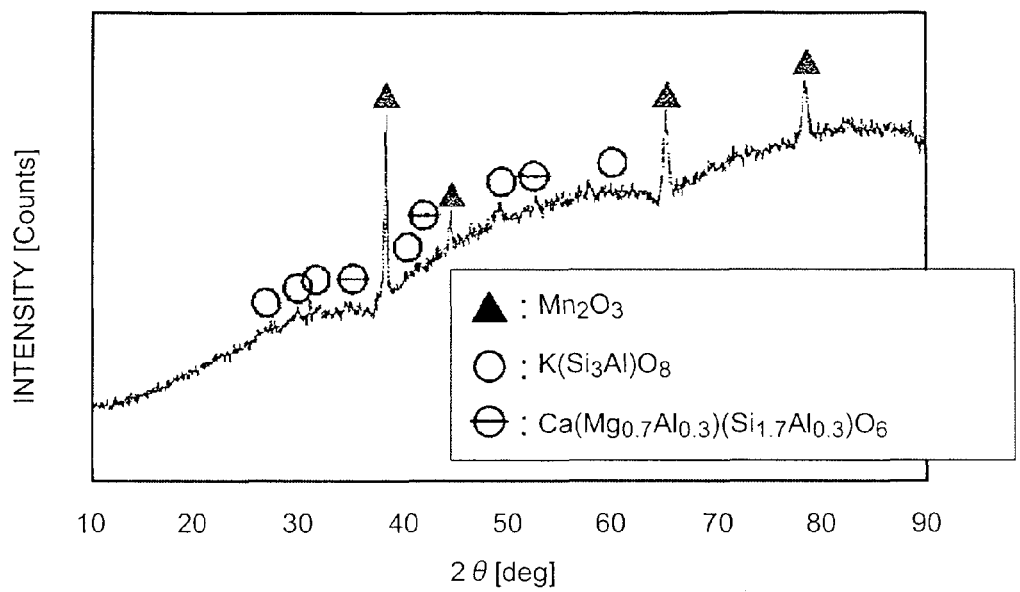
FIG. 2 is a diagram illustrating an X-ray diffraction pattern, after a Mn endurance test, of a glass coating film according to Example 1.
Figure 3:
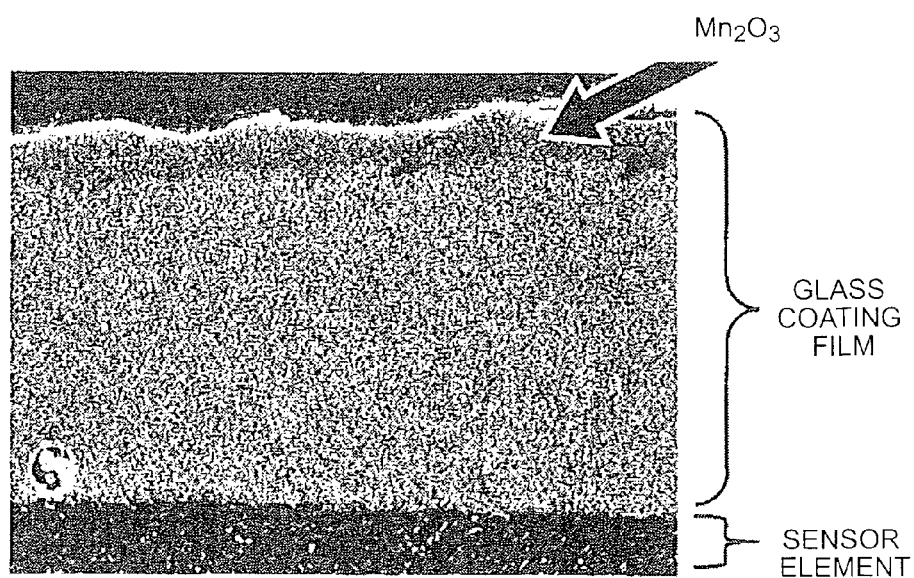
FIG. 3 is a scanning electron microscopy (SEM) image of a cross-section, after a Mn endurance test, of the exhaust gas sensor according to Example 1.

The gas sensor 100 thus obtained was subjected to a Mn endurance test. The Mn endurance test was performed by applying Mn$_3$O$_4$ powder onto the glass coating film 20, followed by firing at 800° C. for 24 hours. FIG. 2 illustrates an X-ray diffraction pattern after the Mn endurance test. FIG. 3 illustrates a SEM image of a cross-section of the sensor element 10 after the Mn endurance test.

As illustrated in FIG. 2, diffraction peaks attributable to Mn$_3$O$_4$ particles were observed among broad peaks derived from amorphous materials in the glass coating film 20. This indicated that the glass coating film component and Mn$_3$O$_4$ were in an unreacted state. As illustrated in FIG. 3, the surface layer portion of the glass coating film 20 exhibited discoloration, which suggested that Mn$_3$O$_4$ particles had been incorporated into the surface layer portion of the glass coating film 20 through solid-phase diffusion.

Figure 4:
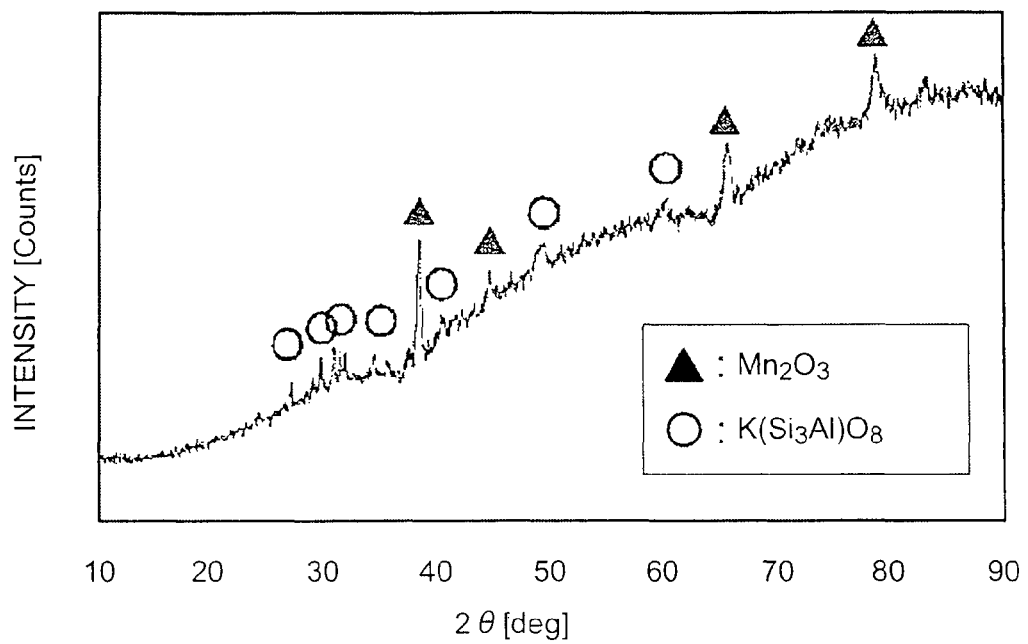
FIG. 4 is a diagram illustrating an X-ray diffraction pattern, after a Mn endurance test, of a glass coating film according to Example 2.
Figure 5:
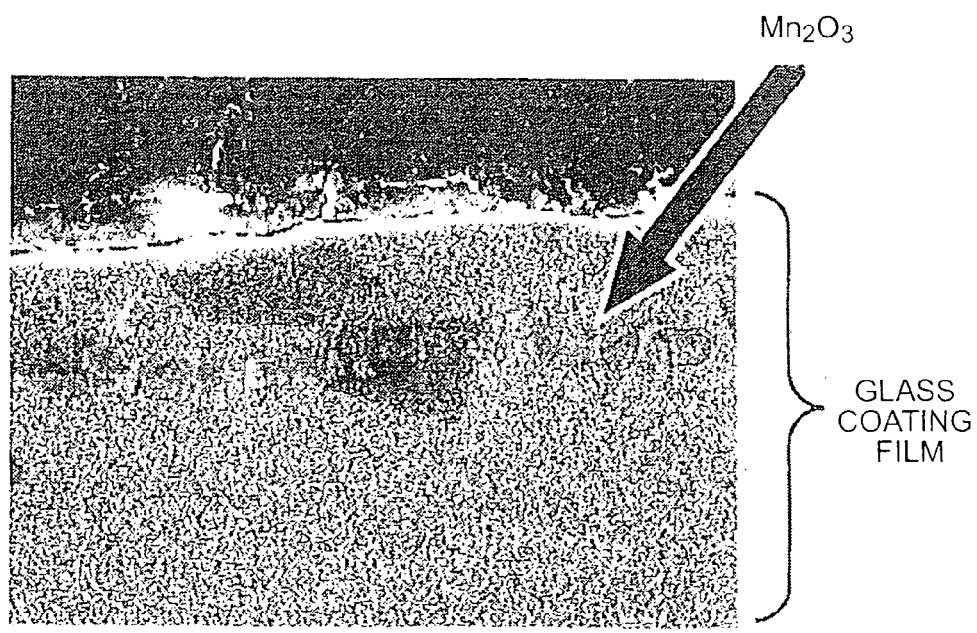
FIG. 5 is a SEM image of a cross-section, after a Mn endurance test, of the exhaust gas sensor according to Example 2.

In Example 2, a gas sensor 100 was produced in the same way as in Example 1 but herein the composition of the glass coating film 20 was modified as given in Tables 2-1 and 2-2. The gas sensor 100 was subjected to an Mn endurance test in the same way as in Example 1. FIG. 4 illustrates an X-ray diffraction pattern of the glass coating film made up of the borosilicate glass after the abovementioned Mn endurance test. FIG. 5 illustrates a SEM image of a cross-section of the sensor element 10 after the Mn endurance test.

TABLE 2-1

| Composition (mass %) | | | | | | | |
|---|---|---|---|---|---|---|---|
| SiO$_2$ | B$_2$O$_3$ | Al$_2$O$_3$ | BaO | Li$_2$O | Na$_2$O | K$_2$O | CaO |
| 33.10 | 14.90 | 3.09 | 24.75 | 0.86 | 0.39 | 5.25 | 0.08 |
| SrO | La$_2$O$_3$ | ZrO$_2$ | SnO | ZnO | NiO | CoO | MoO$_2$ |
| 0.30 | 1.93 | 1.68 | 0.62 | 9.65 | 0.61 | 0.50 | 0.22 |
| Total: 97.93 mass % | | | | | | | |

TABLE 2-2

| Minor component composition (mass %) | | |
|---|---|---|
| MgO | Y$_2$O$_3$ | HfO$_2$ |
| | Total: 2.07 mass % | |

As illustrated in FIG. 4, diffraction peaks attributable to Mn$_3$O$_4$ particles were observed among broad peaks derived from amorphous materials in the glass coating film 20, which suggested that the glass coating film component and Mn$_3$O$_4$ were in an unreacted state. As illustrated in FIG. 5, the interior of the glass coating film 20 exhibited discoloration. This showed that Mn$_3$O$_4$ particles were incorporated into the interior of the glass coating film 20 through solid-phase diffusion.

Figure 6:
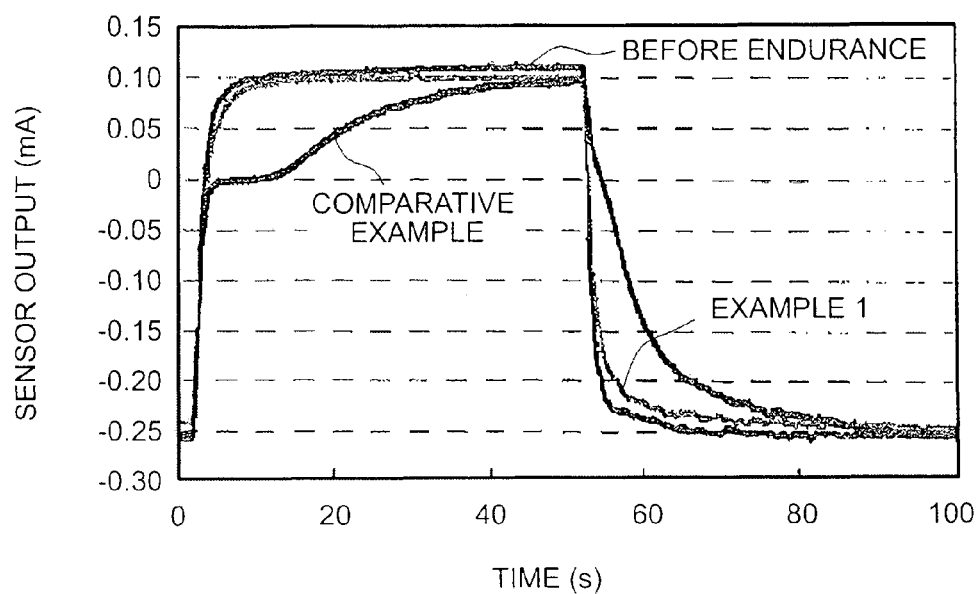
FIG. 6 is a diagram illustrating sensor output waveforms of the exhaust gas sensor according to Example 1.
Figure 7:
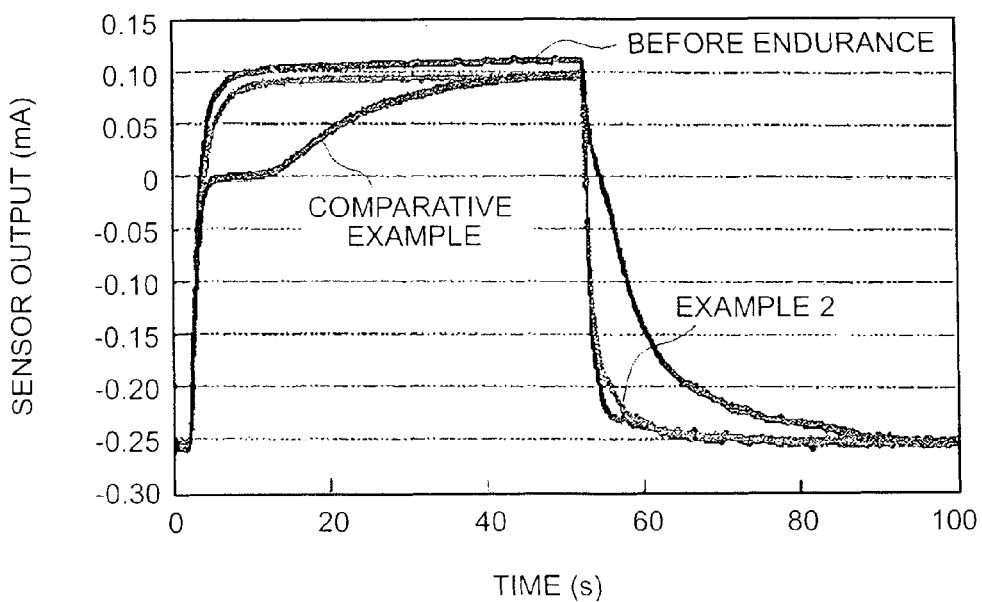
FIG. 7 is a diagram illustrating sensor output waveforms of the exhaust gas sensor according to Example 2.

Sensor output waveforms after the above-described Mn endurance test ware measured for the gas sensors of Examples 1 and 2. The sensor output waveforms were measured by assembling each gas sensor onto a gas detector, and holding the sensor in a test gas having a predetermined oxygen concentration. The sensor output waveforms were measured before and after the above-described Mn endurance test. FIG. 6 illustrates sensor output waveforms, before and after an Mn endurance test, in Example 1. FIG. 7 illustrates sensor output waveforms, before and after an Mn endurance test, in Example 2.

For comparison purposes, a gas sensor was prepared in which no glass coating film 20 was formed. The Mn endurance test was carried out then by applying Mn$_3$O$_4$ powder onto the sensor element 10, followed by firing at 800° C. for 24 hours. The sensor response output waveform after the Mn endurance test was measured in the same way as in Examples 1 and 2.

As FIG. 6 and FIG. 7 show, the sensor output waveforms in Examples 1 and 2, in which the glass coating film 20 made up of borosilicate glass was formed on the surface of the sensor element 10, exhibited virtually no changes before and after the Mn endurance test, and good results were obtained. By contrast, the sensor output response after the Mn endurance test exhibited significant delay with respect to before endurance in the comparative example where the glass coating film 20 made up of borosilicate glass was not formed on the surface of the sensor element 10. It is deemed that the delay in the comparative example arises from the Mn component that is adhered to the sensor element 10. All the above indicated that sensor response delay due to Mn can be eliminated by forming the glass coating film 20, made up of borosilicate glass, on the surface of the sensor element 10.

Figure 8:
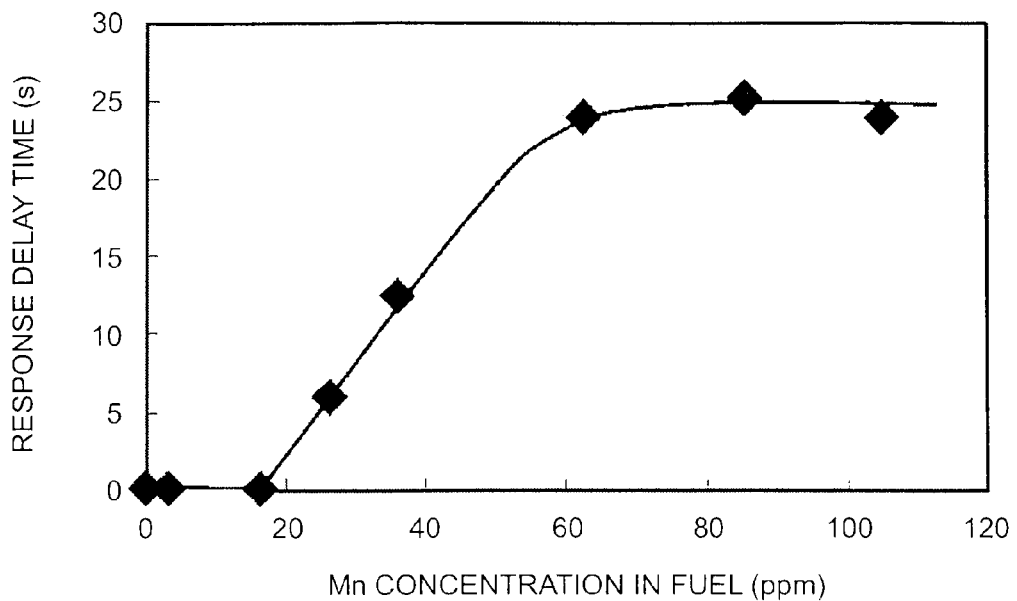
FIG. 8 is a graph illustrating a relationship between Mn concentration in fuel and response delay time.
Figure 9:
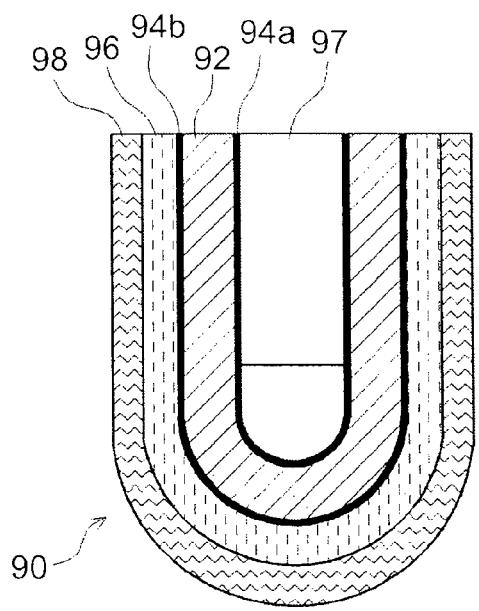
FIG. 9 is a diagram illustrating schematically a gas sensor in the related art.

As a Reference example, the below-described test was performed in order to verify the influence that Mn in fuel exerts on sensor response. In the test, a gas sensor, having no glass coating film formed on the surface of a sensor element, was disposed in the exhaust system of an engine. There was measured the sensor output after endurance involving travel for 150,000 miles (about 240,000 km) using a fuel to which methylcyclopentadienyl manganese tricarbonyl (MMT), as an octane booster, had been added in an arbitrary concentration. The sensor response delay time was assessed through comparison with the sensor output before endurance. The results are depicted in FIG. 8. FIG. 8 is a graph illustrating the relationship between Mn concentration (ppm) in fuel and response delay time (s).

As FIG. 8 shows, the response delay time tended to increase once the Mn concentration in fuel exceeded 20 ppm. In particular, the response delay time reached about 25 seconds as the Mn concentration in fuel exceeded 60 ppm. It is deemed that the Mn component adheres readily onto the sensor element of an exhaust gas sensor that is disposed in the exhaust system of an engine that utilizes fuel having a high Mn concentration, and that sensor response delay due to OSC that accompanies changes in the valence of Mn is likely to occur. Therefore, the exhaust gas sensor 100 of the embodiment of the invention, which allows effectively preventing sensor response delay due to the abovementioned OSC, can be suitably used, in particular, in engines that utilize fuels having a Mn concentration that exceeds 20 ppm, such as the abovementioned ones.

Embodiments of the invention have been explained in detail, but the embodiments are merely exemplary in character, and are not meant to limit the invention in any way. The invention encompasses also all manner of variations and modifications of the embodiments exemplified above.

The invention claimed is:

1. An exhaust gas sensor configured to detect an oxygen concentration or air-fuel ratio in exhaust gas of an internal combustion engine, the exhaust gas sensor comprising:
   a sensor element configured to detect the oxygen concentration or air-fuel ratio in the exhaust gas sensor; and
   a glass coating film formed on at least part of a surface of the sensor element and capable of absorbing a Mn component contained in the exhaust gas at 700° C., wherein
   the internal combustion engine uses a fuel having a Mn concentration in excess of 20 ppm, wherein
   the glass coating film is made up of borosilicate glass containing Si, B, Al, Ba and R as main constituents, wherein R is at least one from among Li, Na and K, mass ratios of main components of the borosilicate glass, in terms of oxide, with an entirety of the borosilicate glass as 100 mass %, are:
$SiO_2$ 30 mass % to 45 mass %;
$B_2O_3$ 10 mass % to 20 mass %;
$Al_2O_3$ 1 mass % to 10 mass %;
BaO 20 mass % to 30 mass %; and
$R_2O$ 2 mass % to 10 mass %, and
a total of the main components is 70 mass % or more.

2. The exhaust gas sensor according to claim 1, wherein the sensor element is formed of a stack of a solid electrolyte layer, a heater layer and a porous diffusion resistance layer,
a pair of electrodes is provided on either side of the solid electrolyte layer,
the heater layer includes a heating element that generates heat through energization,
the diffusion resistance layer lets the exhaust gas through in such a manner that the exhaust gas is introduced into either of the pair of electrodes, and
the glass coating film is formed, on the surface of the sensor element, at a region excluding the diffusion resistance layer.

3. The exhaust gas sensor according to claim 1, wherein the exhaust gas sensor is used in order to detect the oxygen concentration or air-fuel ratio in the exhaust gas of the internal combustion engine that utilizes the fuel having the Mn concentration in excess of 20 ppm.

4. An exhaust gas sensor configured to detect an oxygen concentration or air-fuel ratio in exhaust gas of an internal combustion engine, the exhaust gas sensor comprising:
a sensor element configured to detect the oxygen concentration or air-fuel ratio in the exhaust gas sensor; and
a glass coating film formed on at least part of a surface of the sensor element and capable of absorbing a Mn component contained in the exhaust gas at 700° C., wherein
the internal combustion engine uses a fuel having a Mn concentration in excess of 20 ppm, wherein
the glass coating film is made up of borosilicate glass containing Si, B, Al, Ba and R as main constituents, wherein R is at least one from among Li, Na and K,
mass ratios of main components of the borosilicate glass, in terms of oxide, with an entirety of the borosilicate glass as 100 mass %, are:
$SiO_2$ 30 mass % to 45 mass %;
$B_2O_3$ 10 mass % to 20 mass %;
$Al_2O_3$ 1 mass % to 10 mass %;
BaO 20 mass % to 30 mass %; and
$R_2O$ 2 mass % to 10 mass %, and
a total of the main components is 70 mass % or more and
a value resulting from dividing the mass ratio of $B_2O_3$ by the mass ratio of $SiO_2$ in the borosilicate glass ranges from 0.25 to 0.5.

* * * * *